United States Patent
Sawa

(10) Patent No.: US 8,655,602 B2
(45) Date of Patent: Feb. 18, 2014

(54) HARDNESS TEST METHOD, HARDNESS TESTER, AND COMPUTER-READABLE STORAGE MEDIUM STORING PROGRAM

(75) Inventor: Takeshi Sawa, Kawasaki (JP)

(73) Assignee: Mitutoyo Corporation, Kawasaki-Shi (JP)

( * ) Notice: Subject to any disclaimer, the term of this patent is extended or adjusted under 35 U.S.C. 154(b) by 306 days.

(21) Appl. No.: 13/004,145

(22) Filed: Jan. 11, 2011

(65) Prior Publication Data

US 2011/0178728 A1 Jul. 21, 2011

(30) Foreign Application Priority Data

Jan. 15, 2010 (JP) ................ 2010-006587

(51) Int. Cl.
*G01L 1/00* (2006.01)
*G01N 3/42* (2006.01)

(52) U.S. Cl.
USPC .................. 702/42; 702/41; 73/81

(58) Field of Classification Search
USPC ........................ 702/41, 42; 73/81
See application file for complete search history.

(56) References Cited

U.S. PATENT DOCUMENTS

| 7,424,822 | B2 * | 9/2008 | Isomoto ............................ 73/81 |
| 2003/0060987 | A1 * | 3/2003 | Dao et al. ......................... 702/42 |
| 2005/0154540 | A1 * | 7/2005 | Ma et al. ......................... 702/33 |
| 2009/0044609 | A1 * | 2/2009 | Sawa et al. ....................... 73/81 |

FOREIGN PATENT DOCUMENTS

| EP | 2028472 A2 | 2/2009 |
| JP | 2005-326169 | 11/2005 |
| JP | 2008-197010 | 8/2008 |
| JP | 2009-047427 | 3/2009 |
| RU | 2279056 C1 * | 6/2006 |

OTHER PUBLICATIONS

Zhenghao Gan, Yuebin Zhang, Guoqing Yu, C. M. Tan, S. P. Lau, and B. K. Tay "Intrinsic mechanical properties of diamond-like carbon thin films deposited by filtered cathodic vacuum arc", J. Appl. Phys 95, No. 7 (Apr. 1, 2004), pp. 3509-3515.*
Khudobin, L V. Machine Translation of RU2279056. Jun. 2006.*
Miyahara, et al., "Evaluation of Mechanical Properties in Nanometer Scale Using AFM-based Nanoindentation Tester", Nanostructured Materials, Elsevier, New York, NY. vol. 12, No. 5-8, 4 pages.
European Search Report, EP Application 11150288, dated Jul. 25, 2012, 7 pages.
Japanese Office Action and English Translation, Application No. JP 2010-006587 dated May 15, 2013, 5 pages.

* cited by examiner

*Primary Examiner* — Mohamed Charioui
*Assistant Examiner* — Liam R Casey
(74) *Attorney, Agent, or Firm* — Rankin, Hill & Clark LLP

(57) ABSTRACT

A hardness test method includes a measurement step of forming an indent by indenting a surface of a sample with an indenter loaded with a predetermined load and detecting a displacement quantity of the indenter and a test force loaded on the indenter at a time of forming the indent to measure an indentation curve, a work load calculation step of calculating a work load by plastic deformation (Wp) from an area of an indentation curve obtained by the measurement step, and an estimation calculation step of calculating an estimation (HVe) of Vickers hardness by using the work load (Wp), calculated at the work load calculation step, and a previously determined coefficient K in conformity with $HVe=(K/Wp)^2$.

8 Claims, 11 Drawing Sheets

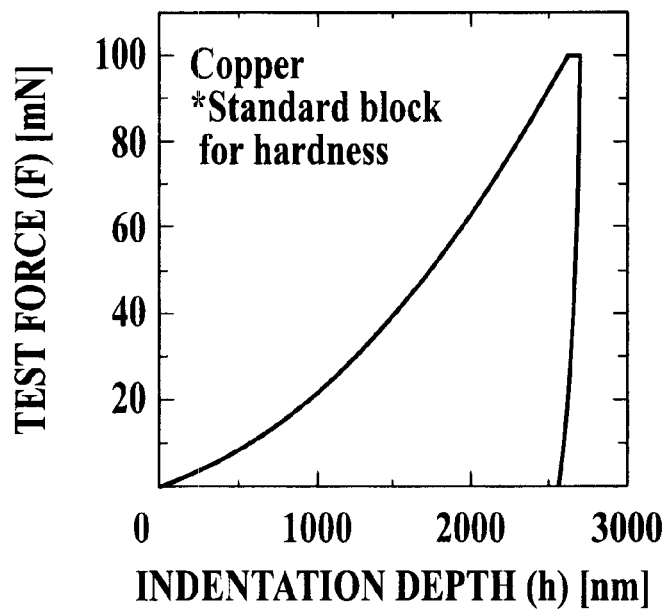
COPPER
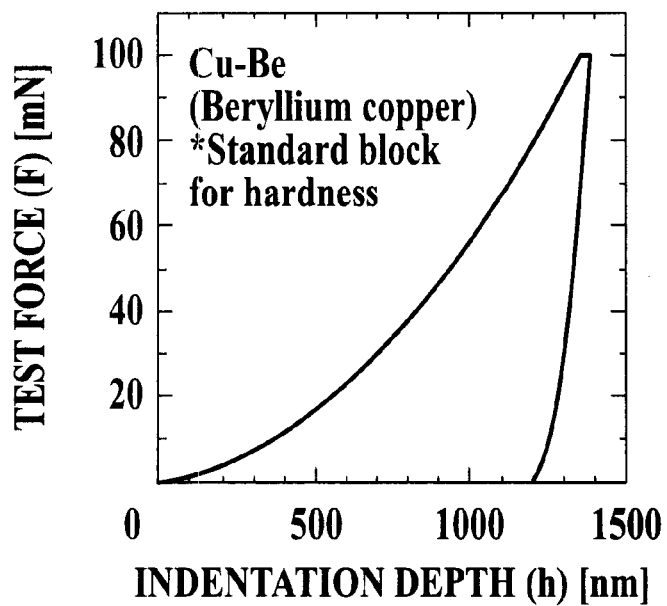
BERYLLIUM COPPER

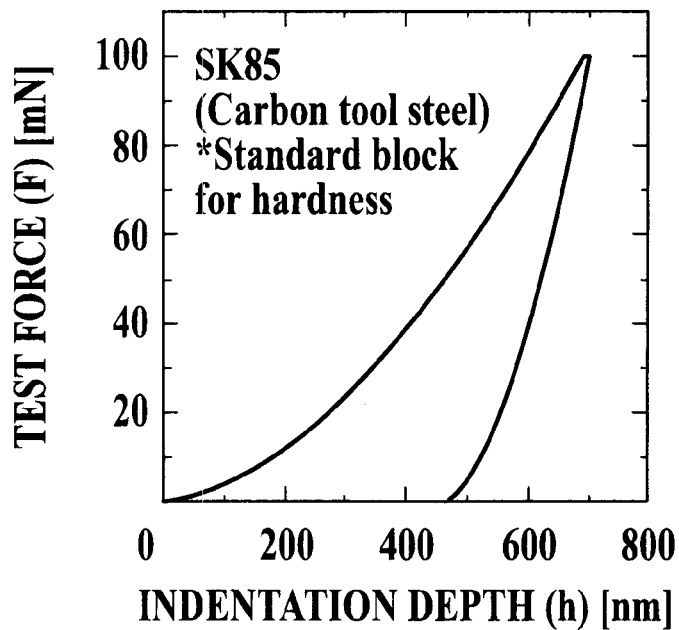
TOOL STEEL
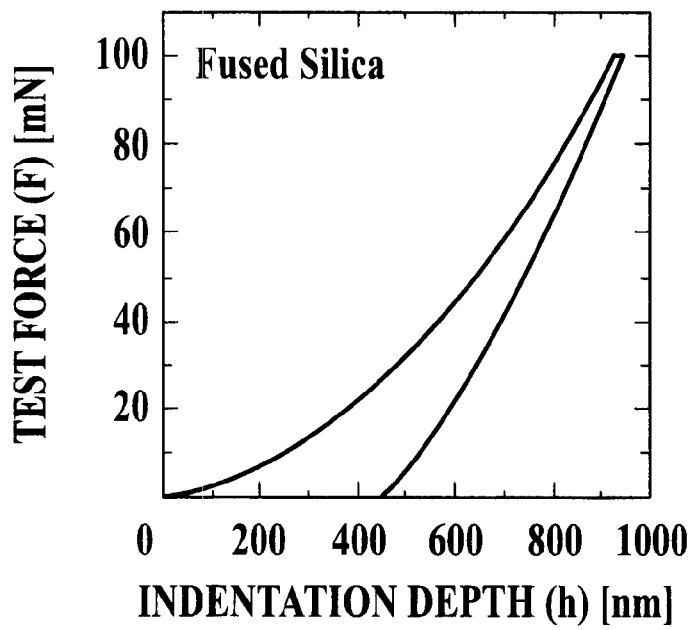
FUSED SILICA

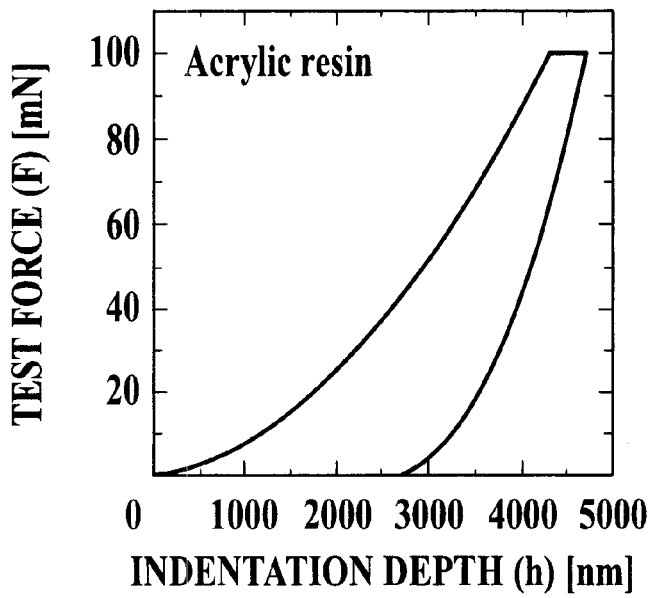
ACRYLIC RESIN
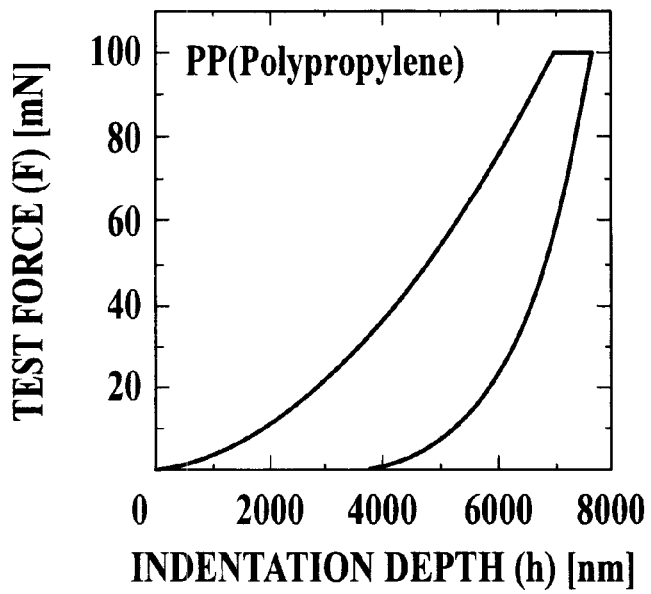
POLYPROPYLENE

DLC FILM

HARDNESS TEST METHOD, HARDNESS TESTER, AND COMPUTER-READABLE STORAGE MEDIUM STORING PROGRAM

BACKGROUND OF THE INVENTION

1. Field of the Invention

The present invention relates to a hardness test method, a hardness tester, and a computer-readable storage medium storing a program.

2. Description of the Related Art

Conventionally, an indentation hardness tester, such as a Vickers hardness tester, for evaluating and measuring the hardness of a sample on the basis of an indent formed by indenting an indenter, loaded with a predetermined load thereon, on a surface of the sample has been known (see, for example, Japanese Patent Application Laid-Open Publication No. 2005-326169).

Moreover, a test method called nanoindentation (instrumentation indentation test) has been known, which method continuously measures a test force (a force loaded on an indenter) F and an indentation depth (a displacement quantity of an indenter) h to obtain a mechanical property of a material by analyzing an obtained indentation curve (F-h curve) in an indentation process in place of the observation of an indent formed after indentation, (see, for example, Japanese Patent Application Laid-Open Publication No. 2009-47427).

The nanoindentation is effective as an evaluation method of a material the indent observation of which is difficult due to a factor, such as a small size of an indent. Consequently, the nanoindentation is noticed to be suitable for the evaluation of the mechanical properties of a plastic and a thin film material, which are construction materials indispensable for various machines and structures.

For the nanoindentation, International Standard ISO (International Organization for Standardization) 14577 regulates the parameter of hardness called indentation hardness $H_{IT}$, and the cases of using the indentation hardness $H_{IT}$ for the evaluation of a thin film material and the like have recently increased. The indentation hardness $H_{IT}$ is treated as a value having a correlation with the Vickers hardness.

Here, the analysis method of the indentation hardness $H_{IT}$ that is regulated by the ISO 14577 is shown.

FIG. 7 is a schematic diagram of an F-h curve. The ordinate axis thereof indicates a test force F, and the abscissa axis thereof indicates an indentation depth h.

The indentation hardness $H_{IT}$ is defined by the following formula (1) as a value obtained by dividing the maximum test force (set test force) Fmax by the contact projected area Ap(hc) of a sample of an indenter at the time of the maximum indentation.

$$H_{IT} = F\text{max}/Ap(hc) \quad (1)$$

Then, for example, the contact projected area Ap(hc) is expressed as the following formula (2) from the geometric shape of the Berkovich indenter.

$$Ap(hc) = 23.96 hc^2 \quad (2)$$

Moreover, hc is called contact depth, and is expressed by the following formula (3) by using the maximum indentation depth hmax, and an intersection point hr of a tangential line of the initial part of a load unloading curve and an indentation depth axis.

$$Hc = h\text{max} - 0.75(h\text{max} - hr) \quad (3)$$

The aforesaid analysis method of the indentation hardness $H_{IT}$ regulated by the ISO 14577 is a technique proposed by Oliver and Phart, and it was ascertained by their research that there was a correlation between the indentation hardness $H_{IT}$ and the Vickers hardness HV.

However, the samples that they used in their research were ones each having a strong tendency of plastic behavior, such as a metal, and ones each expressing a deformation in which an elastic deformation and a plastic deformation were mixed, i.e. ones clearly expressing elastoplastic behavior, such as fused silica, and they did not examine the materials each having a strong tendency of showing the elastic behavior, such as a rubber material and an amorphous material. In the nanoindentation including also the materials each having a strong tendency of showing the elastic behavior as objects, it is difficult to treat the indentation hardness $H_{IT}$ regulated in the ISO 14577 as being equivalent to the Vickers hardness HV.

For example, FIG. 8 is a diagram showing a relation between the indentation hardness $H_{IT}$ and the Vickers hardness HV of copper, beryllium copper (Cu—Be), tool steel (SK85), fused silica, acrylic resin, polypropylene (PP), and a diamond-like carbon (DLC) film. The ordinate axis thereof indicates the indentation hardness $H_{IT}$, and the abscissa axis thereof indicates the Vickers hardness HV.

The straight line in FIG. 8 expresses the indentation hardness $H_{IT}$ and the Vickers hardness HV by the following formula (4) by using a coefficient C.

$$H_{IT} = C_1 \cdot HV \quad (4)$$

To put it concretely, the straight line in FIG. 8 expresses the formula (4) when the coefficient $C_1$ is set to 1.25. In addition, as the reasons why the coefficient $C_1$ is not 1 ($H_{IT} \neq HV$), for example, some causes, such as a point of using a projected area, not a surface area, for the calculation of indentation hardness $H_{IT}$; causes of errors peculiar to the nanoindentation, such as a tip shape of an indenter and a surface detection error; and the like, can be considered. In any event, it can be said that the values of the indentation hardness $H_{IT}$ and the Vickers hardness HV of the samples other than the DLC film have a correlation, although the values are not equal.

On the other hand, the values of the indentation hardness $H_{IT}$ and the Vickers hardness HV of the DLC film greatly deviate from the straight line, and the fact indicates that the treatment of the indentation hardness $H_{IT}$ as being equivalent to the Vickers hardness HV in the regulation of the ISO 14577 has a problem for the DLC film.

That is, the technique for obtaining a value corresponding to the Vickers hardness HV in the nanoindentation is not established in the case where the rubber material, the amorphous material, or the like is used as a sample.

SUMMARY OF THE INVENTION

It is an object of the present invention to provide a hardness test method, a hardness tester, and a computer-readable storage medium storing a program that can obtain an estimation of Vickers hardness, which estimation is a value corresponding to the Vickers hardness, in nanoindentation.

In order to achieve the object, according to a first aspect of the present invention, a hardness test method is provided which hardness test method includes the steps of:

forming an indent by indenting a surface of a sample with an indenter loaded with a predetermined load and detecting a displacement quantity of the indenter and a test force loaded on the indenter at a time of forming the indent to measure an indentation curve;

calculating a work load by plastic deformation (Wp) from an area of an indentation curve obtained by the step of forming the indent; and calculating an estimation (HVe) of Vickers hardness by using the work load (Wp), calculated at the step of calculating the work load, and a previously determined coefficient K in conformity with $$HVe=(K/Wp)^2.$$

Preferably, the sample is made of a material selected from the group consisting of a diamondlike carbon, a silicon rubber, and a natural rubber.

According to a second aspect of the present invention, a hardness tester for forming an indent by indenting a surface of a sample with an indenter loaded with a predetermined load is provided which hardness tester includes:

a measurement section to measure an indentation curve by detecting a displacement quantity of the indenter and a test force loaded on the indenter at a time of forming the indent;

a work load calculation section to calculate a work load by plastic deformation (Wp) from an area of an indentation curve obtained by the measurement section; and an estimation calculation section to calculate an estimation (HVe) of Vickers hardness by using the work load (Wp), calculated by the work load calculation section, and a previously determined coefficient K in conformity with $$HVe=(K/Wp)^2.$$

According to a third aspect of the present invention, a computer-readable storage medium is provided which computer-readable storage medium stores a program for making a computer function as:

a measurement section to measure an indentation curve by forming an indent by indenting a surface of a sample with an indenter loaded with a predetermined load, and by detecting a displacement quantity of the indenter and a test force loaded on the indenter at a time of forming the indent;

a work load calculation section to calculate a work load by plastic deformation (Wp) from an area of an indentation curve obtained by the measurement section; and an estimation calculation section to calculate an estimation (HVe) of Vickers hardness by using the work load (Wp), calculated by the work load calculation section, and a previously determined coefficient K in conformity with $$HVe=(K/Wp)^2.$$

According to the present invention, after measuring an indentation curve, a work load by plastic deformation (Wp) is calculated from an area of the indentation curve, and an estimation (HVe) of Vickers hardness is calculated by using the calculated work load (Wp) and a previously determined coefficient K in conformity with a relational formula: $HVe=(K/Wp)^2$.

Because a work load by plastic deformation (Wp) is a value having a correlation with Vickers hardness independent of the type of a sample, an estimation (HVe) of the Vickers hardness, which estimation is a value corresponding to the Vickers hardness (HV) can be obtained in nanoindentation including materials showing remarkable elastic behavior, such as a rubber material and an amorphous material.

BRIEF DESCRIPTION OF THE DRAWINGS

FIG. 4A is an example of an indentation curve obtained by measuring copper;

FIG. 4B is an example of an indentation curve obtained by measuring beryllium copper;

FIG. 4C is an example of an indentation curve obtained by measuring tool steel;

FIG. 4D is an example of an indentation curve obtained by measuring fused silica;

FIG. 4E is an example of an indentation curve obtained by measuring an acrylic resin;

FIG. 4F is an example of an indentation curve obtained by measuring a polypropylene;

DETAILED DESCRIPTION OF THE PREFERRED EMBODIMENTS

In the following, a hardness tester and a hardness test method according to an embodiment of the present invention will be described in detail with reference to the accompanying drawings.

A hardness tester 100 of the present embodiment is an instrumented indentation test machine capable of continuously monitoring a test force to be given to an indenter 3 and an indentation depth of the indenter 3.

Moreover, the hardness tester 100 of the present embodiment can use, for example, a DLC, a silicon rubber, a natural rubber, and the like as a sample S. That is, the hardness tester 100 can measure an evaporated film; a thin film of a semiconductor material or the like; a surface treated layer; various plastics; various rubbers; microfilaments; brittle materials, such as a glass and a ceramic; micro-electronic parts, and the like.

Figure 1:
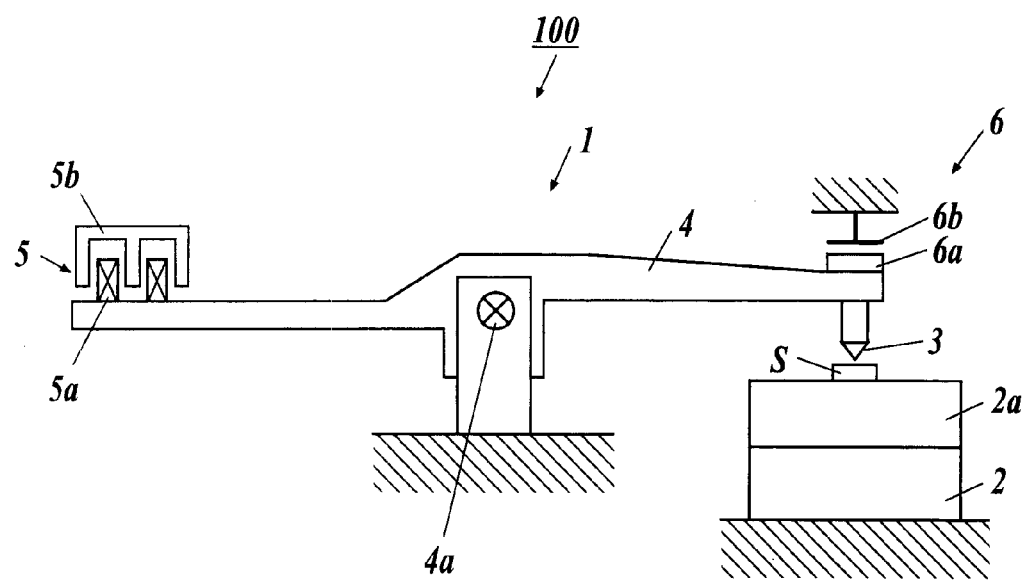
FIG. 1 is a schematic view showing a hardness tester according to an embodiment of the present invention.
Figure 2:
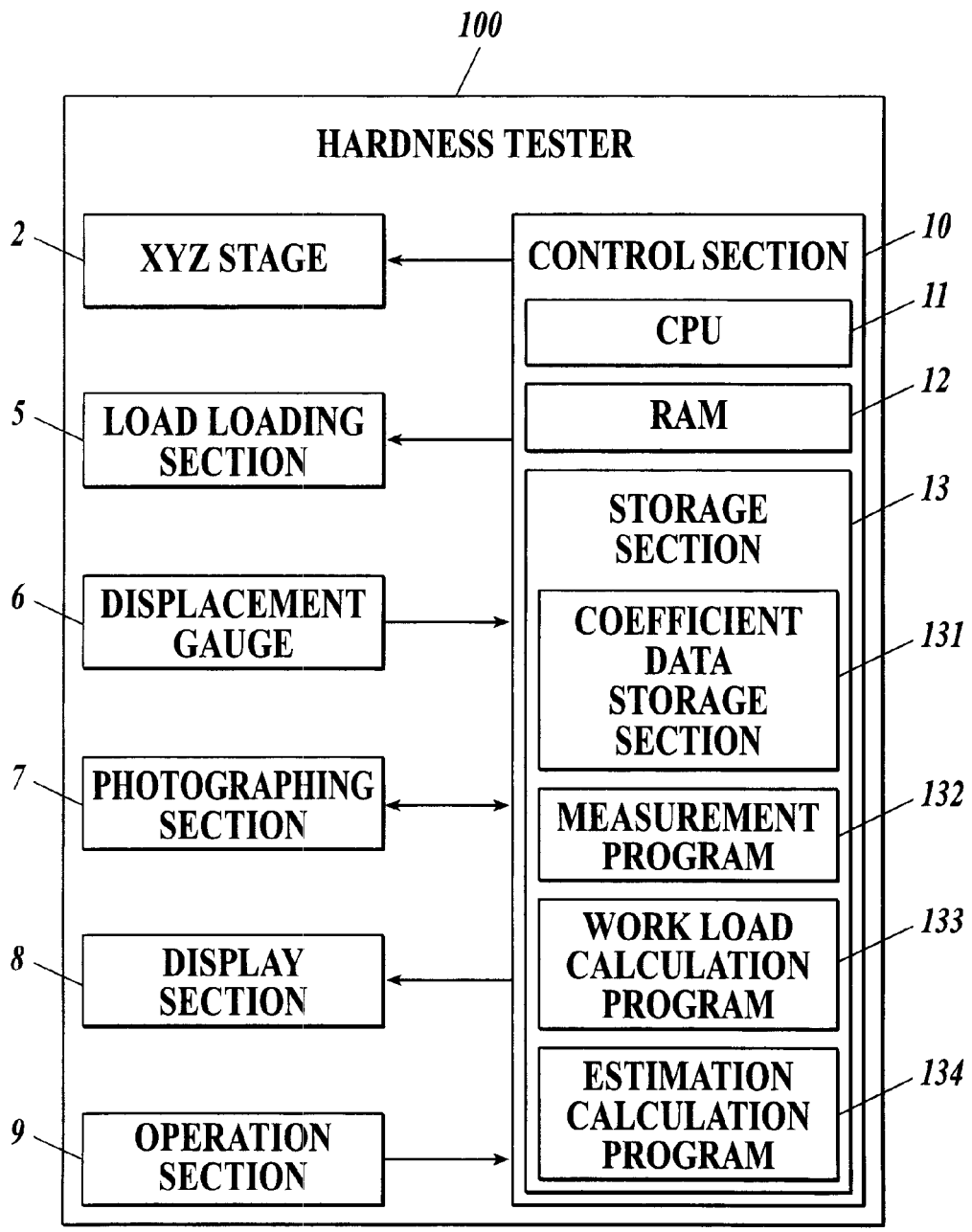
FIG. 2 is a block diagram showing a control configuration of the hardness tester of FIG. 1.

The hardness tester 100 is equipped with a hardness tester main body 1, to which, for example, a control section 10 and each constituent member are provided to be arranged therein as shown in FIGS. 1 and 2. The tester main body 1 is composed of an XYZ stage 2 to move the sample S in X, Y, and Z directions, a load lever 4 including the indenter 3 forming an indent on the sample S at one end thereof, a load loading section 5 to load (give) a predetermined load (test force) to the load lever 4, a displacement gauge 6 to detect a displacement quantity of the indenter 3, a photographing section 7 to photograph an indent or the like formed on the surface of the sample S, a display section 8, an operation section 9, and the like.

The XYZ stage 2 is configured to move into the X, Y, and Z directions (i.e. horizontal direction and vertical direction) in conformity with a control signal input from the control section 10, and the sample S is adapted in such a way that the position thereof to the indenter 3 is adjusted by the movements thereof into front, back, right, left, upper, and lower directions by the XYZ stage 2.

Moreover, the XYZ stage 2 holds the sample S on the sample hold stand 2a lest the sample S placed on the top surface thereof should shifts during test measurement.

The indenter 3 is an indenter used for hardness tests by indent formation, such as, Berkovich, Vickers, Knoop, and Brinell hardness tests. When the indenter 3 is indented on the surface of the sample S by being loaded with a predetermined load, the indenter 3 forms an indent (impression) on the surface of the sample S.

The load lever 4 is, for example, formed in almost a rod, and is fixed on a pedestal at almost the central part through a cross spring 4a.

At one end of the load lever 4, the indenter 3 is provided, which indenter 3 is provided in a freely touchable and detachable state to the sample S from above the sample S placed on the hold stand 2a and is pressed against the surface of the sample S to form an indent on the surface of the sample S.

Moreover, at the other end of the load lever 4, a force coil 5a, constituting the load loading section 5, is provided.

The load loading section 5 is, for example, a force motor, and is composed of the force coil 5a attached to the load lever 4, a fixed magnet 5b fixed to be opposed to the force coil 5a, and the like.

The load loading section 5, for example, rotates the load lever 4 by using a force as a drive force which force is generated by the electromagnetic induction. The electromagnetic induction is generated by a magnetic field. The magnetic filed is generated by the fixed magnet 5b in a gap of the load loading section 5 and the current flowing through the force coil 5a set in the gap in conformity with a control signal input from the control section 10. Consequently, the end of the load lever 4 on the side of the indenter 3 inclines downward, and the indenter 3 is indented on the sample S.

The displacement gauge 6 is, for example, a capacitance type displacement sensor, and is composed of a movable pole plate 6a provided to the end of the load lever 4 on the side of the indenter 3, a fixed pole plate 6b fixed to be opposed to the movable pole plate 6a, and the like.

The displacement gauge 6, for example, detects a change of the electrostatic capacity between the movable pole plate 6a and the fixed pole plate 6b, and then detects the displacement quantity by which the indenter 3 has moved at the time of forming an indent on the sample S (the indentation depth when the indenter 3 is indented into the sample S). The displacement gauge 6 thereby outputs a displacement signal based on the detected displacement quantity to the control section 10.

In addition, although the capacitance type displacement sensor has been illustrated as the displacement gauge 6, the displacement gauge 6 is not limited to this type, but, for example, an optical displacement sensor or an eddy current displacement sensor may be used.

The photographing section 7 is, for example, equipped with a camera and the like, and, for example, photographs an indent and the like formed on the surface of the sample S by the indenter 3 on the sample hold stand 2a in accordance with a control signal input from the control section 10.

The display section 8 is, for example, a liquid display panel, and performs display processing of a surface image of the sample S photographed by the photographing section 7, various test results, and the like in conformity with a control signal input from the control section 10.

The operation section 9 is, for example, an operation key group, such as a keyboard. When the operation section is operated by a user, the operation section outputs an operation signal accompanying the operation to the control section 10. In addition, the operation section 9 may be equipped with the other operation devices, such as a pointing device, such as a mouse and a touch panel, and a remote controller.

The operation section 9 is operated in the case where a user performs an instruction input for performing a hardness test of the sample S, in the case where the user sets a test force, i.e. a load, to be loaded on the indenter 3, and in the other cases.

The control section 10 is composed of a central processing unit (CPU) 11, a random access memory (RAM) 12, a storage section 13, and the like, and is connected to the XYZ stage 2, the load loading section 5, the displacement gauge 6, the photographing section 7, the display section 8, the operation section 9, and the like through a system bus and the like.

The CPU 11, for example, performs various pieces of control processing in conformity with various processing programs for a hardness tester, stored in the storage section 13.

The RAM 12 is provided with, for example, a program storage region for expanding a processing program to be executed by the CPU 11 and the like; a data storage region for storing input data, a processing result generated at the time of the execution of a processing program, and the like.

The storage section 13 stores, for example, a system program executable in the hardness tester 100, various processing programs executable on the system program, the data to be used at the time of executing the various processing programs, the data of various processing results of the operation processing by the CPU 11, and the like. In addition, the programs are stored in the storage section 13 in the form of computer readable program codes.

To put it concretely, the storage section 13 stores, for example, a coefficient data storage section 131, a measurement program 132, a work load calculation program 133, an estimation calculation program 134, and the like.

The coefficient data storage section 131 stores, for example, a coefficient K, which has been set and registered in advance by a user. The coefficient K is a predetermined constant satisfying a formula (6) to be described later, and is obtained by a user beforehand and is previously registered.

To put it concretely, for example, as for several samples, such as fused silica, tool steel, beryllium copper, and copper, their Vickers hardness HV and work loads (Wplastic: hereinafter referred to Wp) by plastic deformation in conformity with a formula (5) to be described later in a certain test force are obtained, and the obtained two values are applied to a formula (8) to be described later. The thus obtained value can be used as the coefficient K.

Moreover, different values of the coefficient K are used correspondingly to the test forces loaded on the indenter 3. If the values of the coefficient K are once registered, the operation of setting and registering the values again is unnecessary.

The measurement program 132 is, for example, a program for enabling the CPU 11 to realize the function of detecting the displacement quantity of the indenter 3 and the test force loaded on the indenter 3 at the time of forming an indent to measure an indentation curve.

Figure 3:
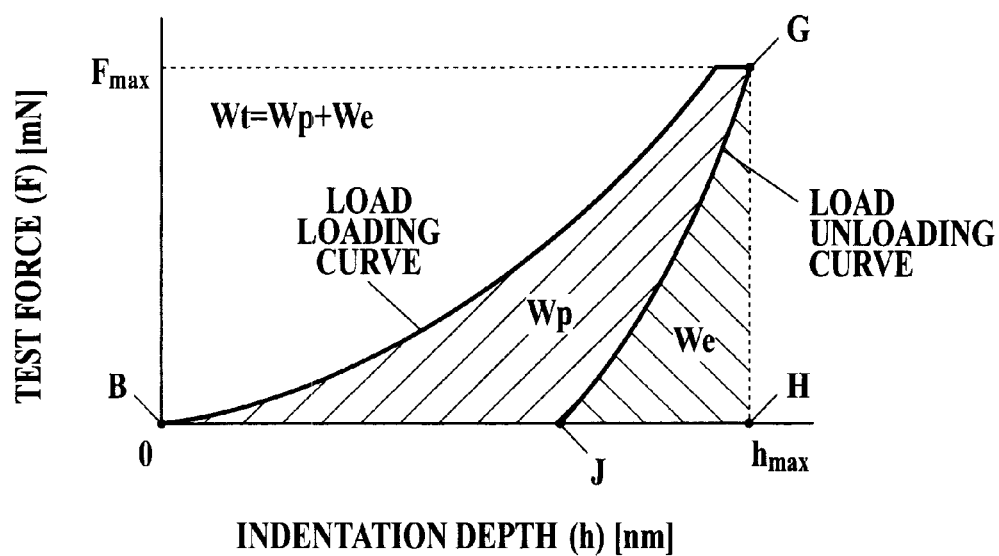
FIG. 3 is a diagram for describing a method of calculating a work load by plastic deformation Wp.
Figure 4G:
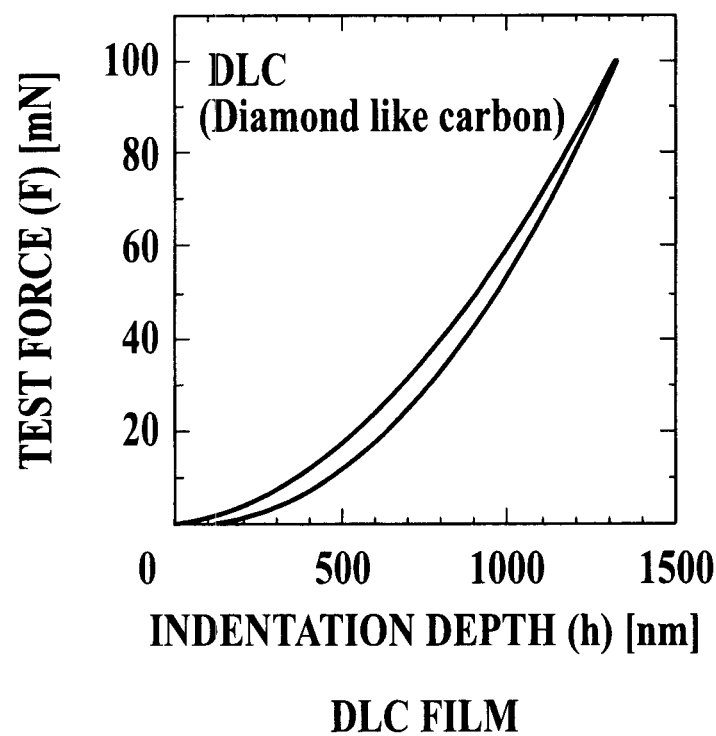
FIG. 4G is an example of an indentation curve obtained by measuring a DLC film.

To put it concretely, when the CPU 11 receives, for example, an input of an operation signal instructing the performance of measurement from the operation section 9, the CPU 11 controls the load loading section 5 to give a predetermined test force to the sample S placed on the sample hold stand 2a. Then, the CPU 11, for example, continuously measures an indentation depth on the sample S of the indenter 3 at the time of forming the indent, and a test force at the time of forming the indent, and measures a test force-indentation depth curve (indentation curve) as shown in FIG. 3.

To put it more concretely, first, when the sample S is placed on the sample hold stand 2a and an operation signal is input, the CPU 11 outputs a control signal to the load loading section 5, and rotates the load lever 4 by using a force generated by electromagnetic induction of a magnetic field generated in the gap by the fixed magnet 5b of the load loading section 5 and a current flowing through the force coil 5a set in the gap, as a drive force. Thereby, the end of the load lever 4 on the side of the indenter 3 inclines downward, and the indenter 3 forms an indent on the sample S.

At the time of forming an indent, the load to be loaded on the indenter 3 is gradually increased until the test force reaches a set maximum test force (load loading step). The test force loaded on the indenter 3 is increased as shown in a load loading curve of FIG. 3 at the load loading step, and thereby the indentation depth of the indenter 3 to the sample S also increases.

Next, when the CPU 11 judges that the load loaded on the indenter 3 reaches the maximum test force, the CPU 11 controls the supply quantity of the current to the drive coil to operate the load loading section 5, and thereby gradually decreases the load loaded on the indenter 3 (load unloading step). In the load unloading step, the test force loaded on the indenter 3 is decreased as shown in the load unloading curve of FIG. 3, and the indent depth of the indenter 3 to the sample S is also decreased.

FIGS. 4A-4G severally show an example of the indentation curves of the results of the measurements of copper, beryllium copper (Cu—Be), tool steel (SK85), fused silica, acrylic resin, polypropylene (PP), and a DLC film.

The CPU 11 functions as a measurement section by executing the measurement program 132.

The work load calculation program 133 is, for example, a program for enabling the CPU 11 to realize the function of calculating the work load by plastic deformation Wp from the area of the indentation curve obtained by the execution of the measurement program 132.

Here, as shown in FIG. 3, the mechanical work load (Wtotal: hereinafter referred to as Wt) generated during the indentation of the indenter 3 to the sample S, a work load (Welastic: hereinafter referred to as We) generated by the elastic deformation occupying the mechanical work load (Wt), and the work load by plastic deformation Wp can be obtained from the indentation curve as follows.

Wt=an area of a part enclosed by a curve passing through the points B and G, and a point H Wp=an area of a part enclosed by a curve passing through the points B, G, and J We=an area of a part enclosed by a curve passing through the points J and G, and a point H Moreover, each work (Wt, Wp, We), i.e. the area of each part, is expressed by the sum of the product of a test force and an indentation depth in a minute interval of the indentation depth as the following formula (5).

$$W = \int F dh \tag{5}$$

The CPU 11 executes the operation of the formula (5) by executing the work load calculation program 133 to calculate the area enclosed by the curve passing through the points B, G, and J in the indentation curve, i.e. the work load by plastic deformation Wp.

The CPU 11 functions as a work load calculation section by executing the work load calculation program 133.

The estimation calculation program 134 is, for example, a program for enabling the CPU 11 to realize the function of calculating an estimate value (HVestimation: hereinafter referred to HVe) of the Vickers hardness by using the work load (Wp) calculated by the execution of the work load calculation program 133 and the previously determined coefficient K in conformity with the following formula (6).

$$HVe=(K/Wp)^2 \tag{6}$$

To put it concretely, the CPU 11 calculates the estimation (HVe) of the Vickers hardness by executing the operation of the formula (6) by using the work load by plastic deformation Wp calculated by the operation of the formula (5), and the coefficient K previously set and registered in the coefficient data storage section 131.

The CPU 11 functions as an estimation calculation section by executing the estimation calculation program 134.

Here, how the formula (6) has been introduced is described.

In the formula (5), when a certain test force is loaded, the work load by plastic deformation Wp is in proportion to the depth of the plastic deformation, i.e. the depth h of an indent.

Because the indent area A in a Vickers test is in proportion to the square of the deformation depth, the following formula (7) comes into effect among a certain coefficient $C_2$, the work load by plastic deformation Wp, and the indent area A.

$$Wp=C_2\sqrt{A} \tag{7}$$

Furthermore, because the Vickers hardness is obtained by dividing the test force F by the indent area A, the following formula (8) comes into effect when the formula (7) is expressed by using the Vickers hardness HV.

$$W_p = K\frac{1}{\sqrt{HV}} \tag{8}$$

Then, if the Vickers hardness HV of the formula (8) is replaced with the estimation HVe of the Vickers hardness HV, the formula (6) comes into effect.

$$HVe=(K/Wp)^2 \tag{6}$$

Figure 5:
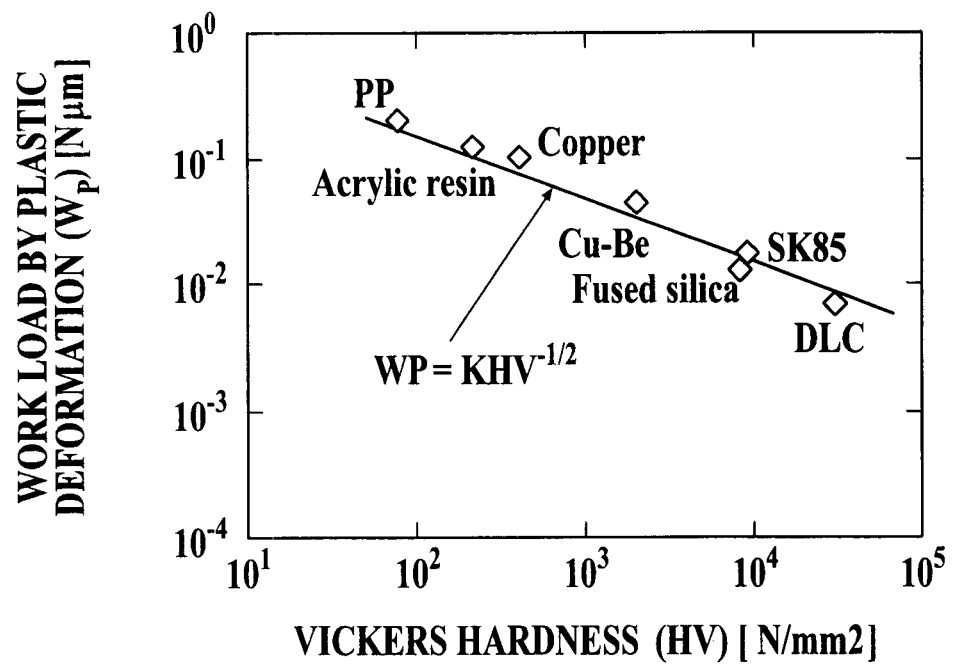
FIG. 5 is a diagram showing a relation between a work load by plastic deformation Wp and Vickers hardness HV.

FIG. 5 is a diagram showing a relation between the work load by plastic deformation Wp and the Vickers hardness HV values obtained by analyzing the indentation curve of FIGS. 4A-4G. In FIG. 5, the ordinate axis indicates the work load by plastic deformation Wp, and the abscissa axis indicates the Vickers hardness HV.

Moreover, the straight line of FIG. 5 expresses the work load by plastic deformation Wp and the Vickers hardness HV with the formula (8) by using the coefficient K.

From FIG. 5, it is known that there is a correlation between the work load by plastic deformation Wp and the Vickers hardness HV to all of the samples S including the DLC film.

That is, it is known that the work load by plastic deformation Wp is effective if used at the time of evaluating the correlation with the Vickers hardness HV.

Figure 6:
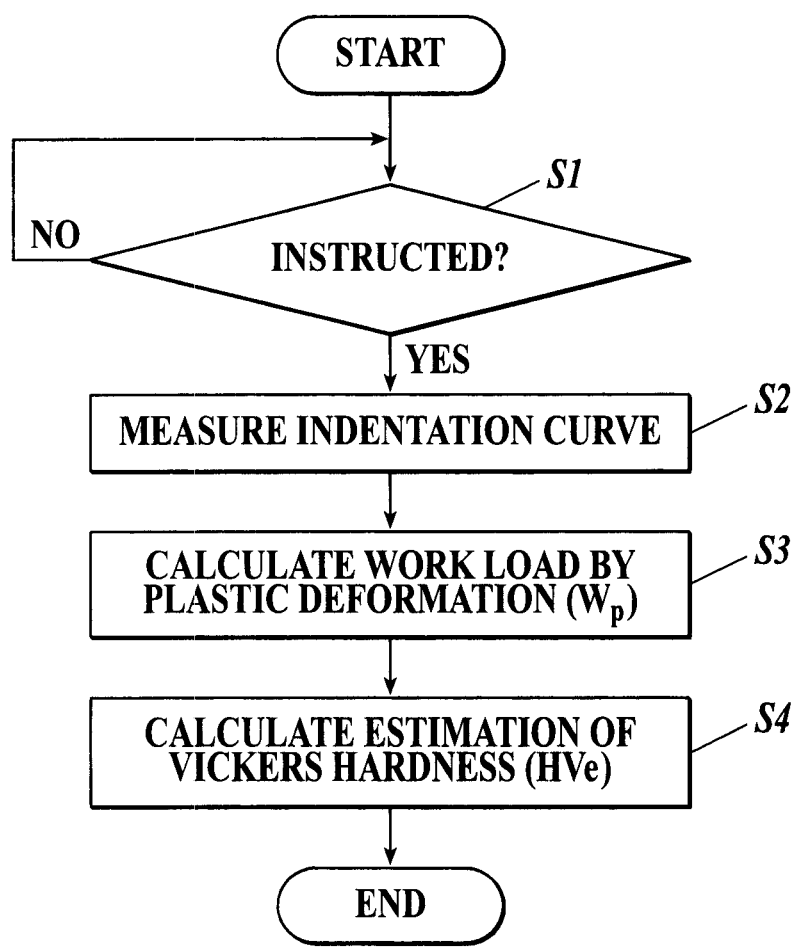
FIG. 6 is a flow chart for describing a hardness test method by the hardness tester of FIG. 1.
Figure 7:
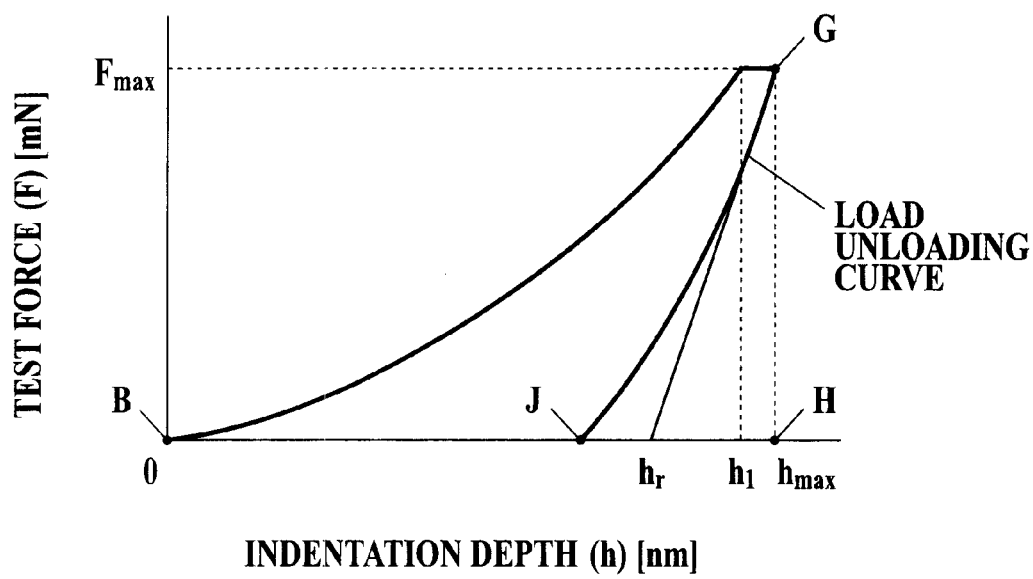
FIG. 7 is a schematic diagram showing an indentation curve.
Figure 8:
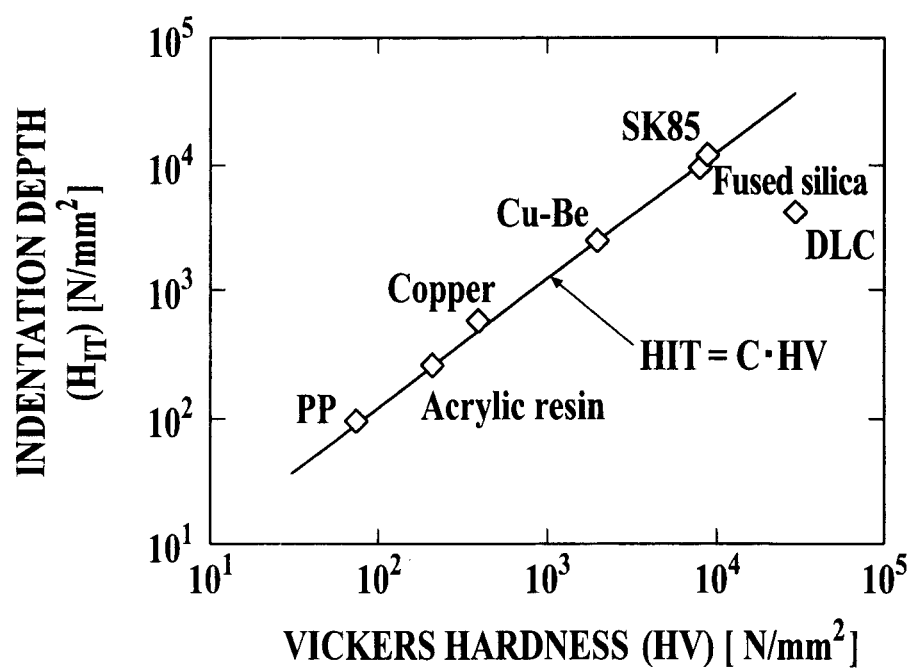
FIG. 8 is a diagram showing a relation between indentation hardness $H_{IT}$ and Vickers hardness HV.

FIG. 6 is a flow chart showing a hardness test method by the hardness tester 100.

First, at Step S1, the CPU 11 judges whether or not a user has instructed to perform the hardness test of the sample S by an operation of the operation section 9. When the CPU 11 judges that the user does not instruct (Step S1: No), the CPU 11 repeats the processing at Step S1.

On the other hand, if the CPU 11 judges that the user has instructed (Step S1: Yes), the CPU 11 measures an indentation curve by executing the measurement program 132 at the succeeding Step S2.

Next, at Step S3, the CPU 11 calculates the work load by plastic deformation Wp form the indentation curve by executing the work load calculation program 133.

Next, at Step S4, the CPU 11 calculates the estimation HVe of the Vickers hardness HV by using the work load by plastic deformation Wp and the previously determined coefficient K by executing the estimation calculation program 134, and ends the present processing.

As described above, according to the hardness tester 100 and the hardness test method of the present embodiment, after measuring an indentation curve, the work load by plastic deformation Wp is calculated from the area of the indentation curve, and the estimation HVe of the Vickers hardness HV is calculated by using the calculated work load Wp and the previously determined coefficient K in conformity with the relational formula: $HVe=(K/Wp)^2$.

Because the work load by plastic deformation Wp is a value having a correlation with the Vickers hardness HV even in the case where the DLC film and the like are used as samples, the estimation HVe of the Vickers hardness HV, which is a value corresponding to the Vickers hardness HV, can be obtained in nanoindentation including the materials expressing remarkable elastic behavior, such as a rubber material and an amorphous material, as objects.

Moreover, according to the hardness tester 100 and the hardness test method of the present embodiment, the sample S is made of a diamondlike carbon, a silicon rubber, or a natural rubber.

Consequently, the hardness tester 100 can measure an evaporated film; a thin film made of a semiconductor material or the like; a surface treated layer; various plastics; various rubbers; brittle materials, such as a microfilament, a glass, and a ceramic; micro electronic parts; and the like.

In addition, the present invention is not limited to the embodiment described above, but can suitably be changed without departing from the spirit and scope of the invention.

For example, the hardness tester may be configured to move the indenter axis into the axial direction thereof by a drive force generated by supplying a drive current to the drive coil.

All of the disclosed contents including the description, the claims, the drawings, and the abstract of Japanese Patent Application No. 2010-006587, filed Jan. 15, 2010 are hereby incorporated by reference herein in its entirety.

While the present invention has been described by illustrating various exemplary embodiments, it is to be understood that the present invention is not limited to the disclosed exemplary embodiments. The scope of the present invention is consequently limited only by the following claims.

What is claimed is:

1. A hardness test method, comprising the steps of:
    forming an indent by indenting a surface of a first sample with an indenter loaded with a predetermined load and detecting a displacement quantity of the indenter and a test force loaded on the indenter at a time of forming the indent to measure an indentation curve;
    calculating a work load by plastic deformation (Wp) from an area of an indentation curve obtained by the step of forming the indent; and
    calculating an estimation (HVe) of Vickers hardness of the first sample by using the work load (Wp), calculated at the step of calculating the work load, and a previously determined coefficient K in conformity with $HVe=(K/Wp)^2$, wherein the coefficient K is previously determined by an equation $Wp'=K/\sqrt{HV}$, where HV is Vickers hardness of a second sample and Wp' is a work load by plastic deformation of the second sample, the second sample being different from the first sample.
2. The hardness test method according to claim 1, wherein the first sample is made of a material selected from the group consisting of a diamondlike carbon, a silicon rubber, and a natural rubber.
3. A hardness tester comprising:
    an indenter configured to form an indent by indenting a surface of a first sample;
    a gauge configured to detect a displacement quantity of the indenter; and
    a computer processor configured to measure an indentation curve by detecting a displacement quantity of the indenter and a test force loaded on the indenter at a time of forming the indent, to calculate a work load by plastic deformation (Wp) from an area of the indentation curve, and to calculate an estimation (HVe) of Vickers hardness of the first sample by using the work load (Wp) and a previously determined coefficient K in conformity with $HVe=(K/Wp)^2$, wherein the coefficient K is previously determined by an equation $Wp'=K/\sqrt{HV}$, where HV is Vickers hardness of a second sample and Wp' is a work load by plastic deformation of the second sample, the second sample being different from the first sample.
4. A non-transitory computer-readable storage medium storing a program for enabling a computer to function as:
    a measurement section to measure an indentation curve by forming an indent by indenting a surface of a first sample with an indenter loaded with a predetermined load, and by detecting a displacement quantity of the indenter and a test force loaded on the indenter at a time of forming the indent;
    a work load calculation section to calculate a work load by plastic deformation (Wp) from an area of an indentation curve obtained by the measurement section; and
    an estimation calculation section to calculate an estimation (HVe) of Vickers hardness of the first sample by using the work load (Wp), calculated by the work load calculation section, and a previously determined coefficient K in conformity with $HVe=(K/Wp)^2$, wherein the coefficient K is previously determined by an equation $Wp'=K/\sqrt{HV}$, where HV is Vickers hardness of a second sample and Wp' is a work load by plastic deformation of the second sample, the second sample being different from the first sample.
5. The hardness test method according to claim 1, wherein calculating the work load by plastic deformation (Wp) of the first sample from the area of the indentation curve comprises summing a product of a test force and an indentation depth in an interval of the indentation depth.
6. The hardness test method according to claim 1, wherein
    the first sample is made of a material selected from the group consisting of a diamondlike carbon, a silicon rubber, and a natural rubber; and
    the second sample is made of a material selected from the group consisting of fused silica, steel, beryllium copper, and copper.
7. The hardness tester according to claim 3, wherein
    the first sample is made of a material selected from the group consisting of a diamondlike carbon, a silicon rubber, and a natural rubber; and
    the second sample is made of a material selected from the group consisting of fused silica, steel, beryllium copper, and copper.
8. The non-transitory computer-readable storage medium according to claim 4, wherein
    the first sample is made of a material selected from the group consisting of a diamondlike carbon, a silicon rubber, and a natural rubber; and the second sample is made of a material selected from the group consisting of fused silica, steel, beryllium copper, and copper.

* * * * *